US008272382B2

(12) United States Patent
Howard et al.

(10) Patent No.: US 8,272,382 B2
(45) Date of Patent: Sep. 25, 2012

(54) HEADGEAR CONNECTION ASSEMBLY

(75) Inventors: Scott Alexander Howard, Harbord (AU); Philip Thomas Stallard, Denistone East (AU)

(73) Assignee: ResMed Limited, Bella Vista (AU)

( * ) Notice: Subject to any disclaimer, the term of this patent is extended or adjusted under 35 U.S.C. 154(b) by 808 days.

(21) Appl. No.: 11/898,074

(22) Filed: Sep. 7, 2007

(65) Prior Publication Data

US 2008/0066759 A1 Mar. 20, 2008

Related U.S. Application Data

(60) Provisional application No. 60/842,650, filed on Sep. 7, 2006.

(51) Int. Cl.
*A62B 18/08* (2006.01)
*A44B 17/00* (2006.01)
(52) U.S. Cl. ............... 128/207.11; 128/206.21; 24/614
(58) Field of Classification Search ............ 128/202.27, 128/205.25, 206.21–206.28, 207.11; 24/614, 24/625, 629
See application file for complete search history.

(56) References Cited

U.S. PATENT DOCUMENTS

| 3,200,461 | A | * | 8/1965 | Miller | 24/665 |
| 4,688,337 | A | * | 8/1987 | Dillner et al. | 24/616 |
| 5,926,928 | A | * | 7/1999 | Lundstedt | 24/625 |
| 6,684,466 | B2 | * | 2/2004 | Nishida et al. | 24/615 |
| 6,817,517 | B2 | * | 11/2004 | Gunther | 235/375 |
| 6,826,806 | B2 | * | 12/2004 | Eaton et al. | 24/115 F |
| 7,024,734 | B2 | * | 4/2006 | Anscher | 24/625 |
| 7,487,772 | B2 | * | 2/2009 | Ging et al. | 128/202.27 |
| 7,556,081 | B2 | * | 7/2009 | Cech | 160/176.1 V |
| 2004/0112384 | A1 | | 6/2004 | Lithgow et al. | |

FOREIGN PATENT DOCUMENTS

WO PCT/AU2006/000037 7/2006
WO PCT/AU2006/000031 4/2007

OTHER PUBLICATIONS

U.S. Appl. No. 10/838,537, filed May 2004, Kwok et al.

* cited by examiner

*Primary Examiner* — Steven Douglas
*Assistant Examiner* — LaToya M Louis
(74) *Attorney, Agent, or Firm* — Nixon & Vanderhye P.C.

(57) ABSTRACT

A headgear connection assembly for a mask assembly includes a pair of clip receptacles provided to respective sides of a mask frame and a pair of locking clips adapted to be removably interlocked with respective clip receptacles. The locking clips are adapted to be removably connected to headgear straps in use. Each clip receptacle includes an upper wall. The upper wall has a recess and a lip adjacent to the recess at the edge of the upper wall.

23 Claims, 14 Drawing Sheets

HEADGEAR CONNECTION ASSEMBLY

CROSS-REFERENCE TO APPLICATIONS

This application claims the benefit of U.S. Provisional Application No. 60/842,650, filed Sep. 7, 2006, which is incorporated herein by reference in its entirety.

Also, PCT Application Nos. PCT/AU2006/000031, filed Jan. 12, 2006, and PCT/AU2006/000037, filed Jan. 12, 2006, are each incorporated herein by reference in its entirety.

Also, U.S. Patent Publication No. US-2004-0112384, published Jun. 17, 2004, is incorporated herein by reference in its entirety.

FIELD OF THE INVENTION

The present invention relates to a headgear connection assembly for use in removably attaching headgear to a frame of a mask assembly used for treatment, e.g., of Sleep Disordered Breathing (SDB) with Continuous Positive Airway Pressure (CPAP) or Non-Invasive Positive Pressure Ventilation (NPPV).

BACKGROUND OF THE INVENTION

A mask assembly typically includes a relatively rigid shell, e.g., a frame, and a patient interface, e.g., a pair of nozzles (which may be in the form of nasal pillows, nasal prongs, cannulae, or nasal puffs) or a cushion (nasal or full-face), that is supported by the rigid shell and structured to deliver pressurized gas to the patient or user in a comfortable, sealed manner. The mask assembly is usually held in place using headgear, the frame and headgear being joined using some form of connector.

Some patients have poor dexterity, and hence find certain arrangements of connectors awkward or difficult to use. Hence, it is important to have a connector which is easy to use and which is easy to correctly assemble.

SUMMARY OF THE INVENTION

One aspect of the present invention relates to a headgear connection assembly for a mask assembly. The headgear connection assembly includes a pair of clip receptacles provided to respective sides of a mask frame and a pair of locking clips adapted to be removably interlocked with respective clip receptacles. The locking clips are adapted to be removably connected to headgear straps in use. Each clip receptacle includes an upper wall. The upper wall has a recess and a lip adjacent to the recess at the edge of the upper wall.

Another aspect of the present invention relates to a headgear connection assembly for a mask assembly. The headgear connection assembly includes a pair of clip receptacles provided to respective sides of a mask frame and a pair of locking clips adapted to be removably interlocked with respective clip receptacles. The locking clips are adapted to be removably connected to headgear straps in use. Each clip receptacle includes an upper wall. The upper wall includes one or more raised ribs.

Another aspect of the present invention relates to a headgear connection assembly for a mask assembly. The headgear connection assembly includes a pair of clip receptacles provided to respective sides of a mask frame and a pair of locking clips adapted to be removably interlocked with respective clip receptacles. The locking clips are adapted to be removably connected to headgear straps in use. Each clip receptacle includes a tapered rib adapted to engage a channel provided in each clip. The rib is inset from an end of the receptacle by about 1.0-2.5 mm.

Another aspect of the present invention relates to a mask assembly for supplying breathable gas to a patient. The mask assembly includes a mask frame, a cushion provided to the mask frame, headgear to maintain the mask frame and cushion in a desired position on the patient's face, and a headgear connection assembly. The headgear connection assembly includes a pair of clip receptacles provided to respective sides of the mask frame and a pair of locking clips adapted to be removably interlocked with respective clip receptacles. The locking clips are adapted to be removably connected to the headgear straps in use. The mask frame includes a relatively smooth external lead-in adjacent an entry point to each clip receptacle.

It will of course be understood that, while embodiments of the present invention will be described in connection with a full facial mask, those in this art will recognize that such a description represents one preferred embodiment and is thus non-limiting. Thus, the structural and/or functional features of the present invention may, for example, also be usefully employed in nasal masks or nasal prongs, nozzles, nare seals, and/or cannulae. Also, the structural and/or functional features of the present invention may be employed in a forehead support of the mask.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-2 show various views of a frame of the mask assembly shown in FIGS. 1-1 to 1-4;

FIG. 2-3 is a cross-sectional view through a headgear connection assembly according to an embodiment of the present invention;

FIGS. 3-1 to 3-2 show various views of a locking clip of the mask assembly shown in FIGS. 1-1 to 1-4;

FIGS. 4-1 to 4-4 show various views of the engagement between the frame and the locking clip of the mask assembly shown in FIGS. 1-1 to 1-4; and FIGS. 5-1 to 5-2 show various views of a frame including a headgear connection assembly according to another embodiment of the present invention.

DETAILED DESCRIPTION OF ILLUSTRATED EMBODIMENTS

Figure 1:
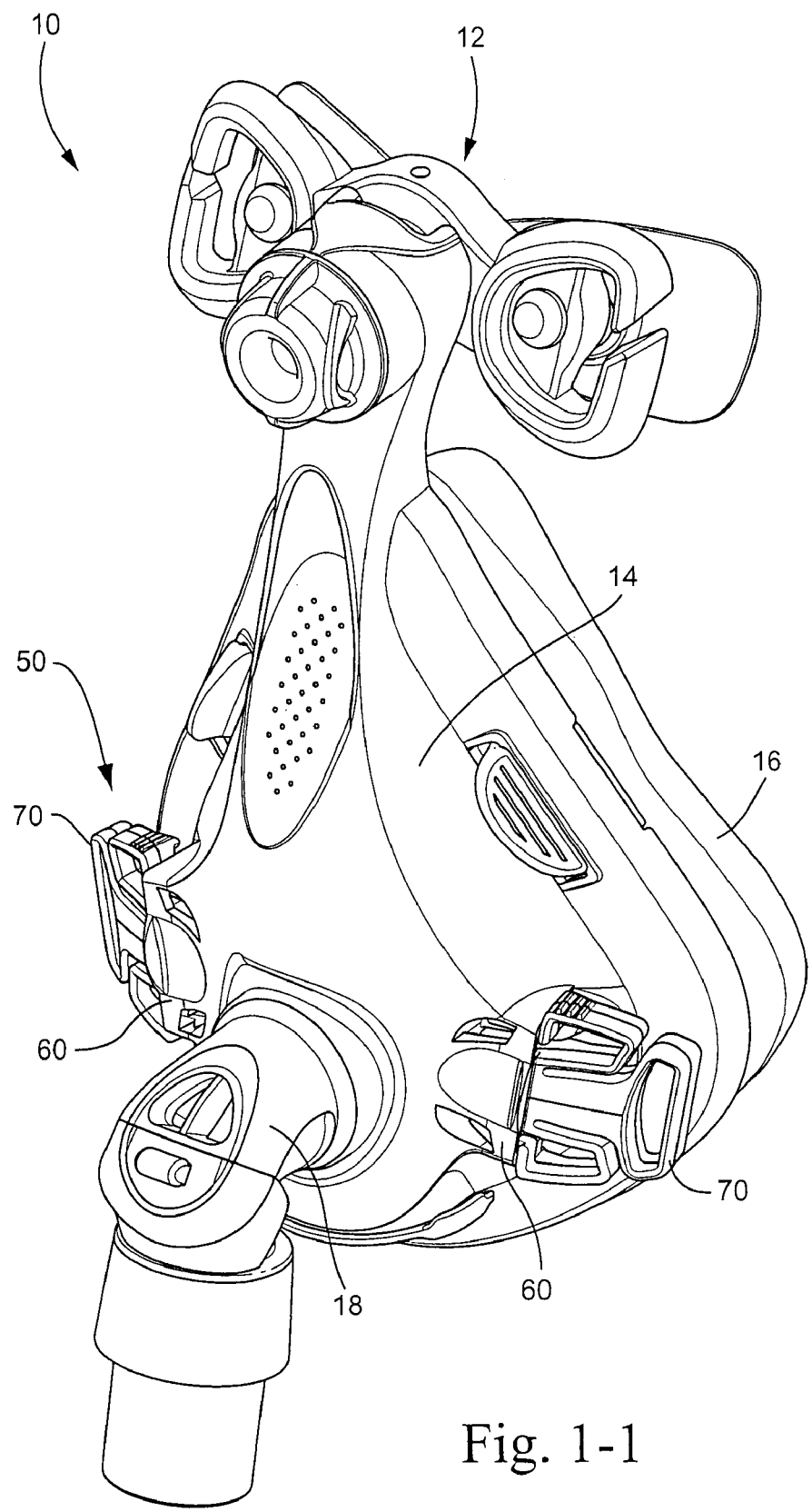
FIGS. 1-1 to 1-4 show various views of a full facial mask assembly including a headgear connection assembly according to an embodiment of the present invention.

Each illustrated embodiment includes features that may be used with the embodiments and/or components described in PCT Application Nos. PCT/AU2006/000031 and PCT/AU2006/000037, as would be apparent to those of ordinary skill in the art. PCT/AU2006/000031 and PCT/AU2006/000037 are each incorporated herein by reference in its entirety.

1. Mask Assembly

FIGS. 1-1 to 1-4 illustrate a full facial mask assembly ("FMA") 10 including a headgear connection assembly 50 according to an embodiment of the present invention. As illustrated, the mask assembly 10 includes a frame 14 (see FIGS. 2-1 to 2-2), a cushion 16 provided to the frame 14 and adapted to form a seal with the patient's face, an elbow assembly 18 provided to the frame 14 and adapted to be connected to an air delivery tube that delivers breathable gas to the patient, and a forehead support 12 to provide a support and stability mechanism between the mask assembly 10 and the patient's forehead. Headgear (not shown) may be removably attached to the frame 14 and the forehead support 12 to maintain the mask assembly 10 in a desired adjusted position on the patient's face. For example, the headgear may include a pair of upper and lower straps with the upper straps removably connected to clip structures provided on the forehead support 16 and the lower straps removably connected to the frame 14 by the headgear connection assembly 50, as will be further discussed below.

Further details and embodiments of this type of mask assembly is disclosed in PCT Application Nos. PCT/AU2006/000031 and PCT/AU2006/000037, the entirety of each incorporated herein by reference. While the headgear connection assembly 50 is described as being implemented into a mask assembly of the type described above, it may be implemented into other mask systems, e.g., full-face mask, mouth mask, nasal mask, nasal prongs, nozzles, nare seals, and/or cannulae. Also, the headgear connection assembly 50 may be implemented into a forehead support of a mask.

2. Headgear Connection Assembly

The headgear connection assembly 50 includes a pair of clip receptacles 60 provided to respective sides of the frame 14 and a pair of locking clips 70 adapted to be removably interlocked with respective clip receptacles 60. The locking clips 70 are removably connected to lower straps of the headgear in use.

One or more aspects of the headgear connection assembly 50 may be similar to that provided on ResMed's ACTIVA® mask. Further details of this headgear connection assembly is disclosed in U.S. Patent Publication No. US-2004-0112384, the entirety of which is incorporated herein by reference.

2.1 Locking Clip

Figures 1, 2:
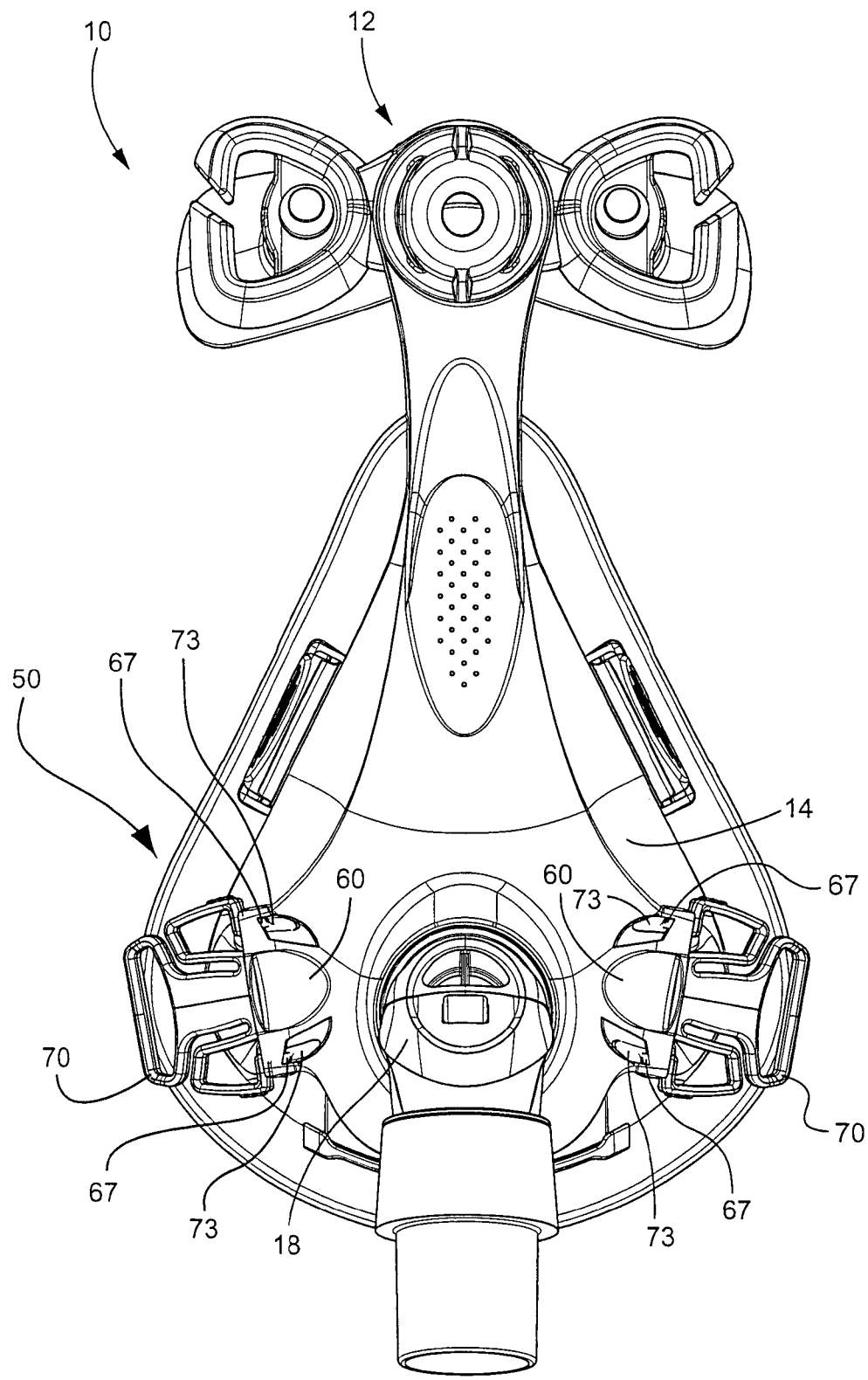
Figures 1, 2, 3:
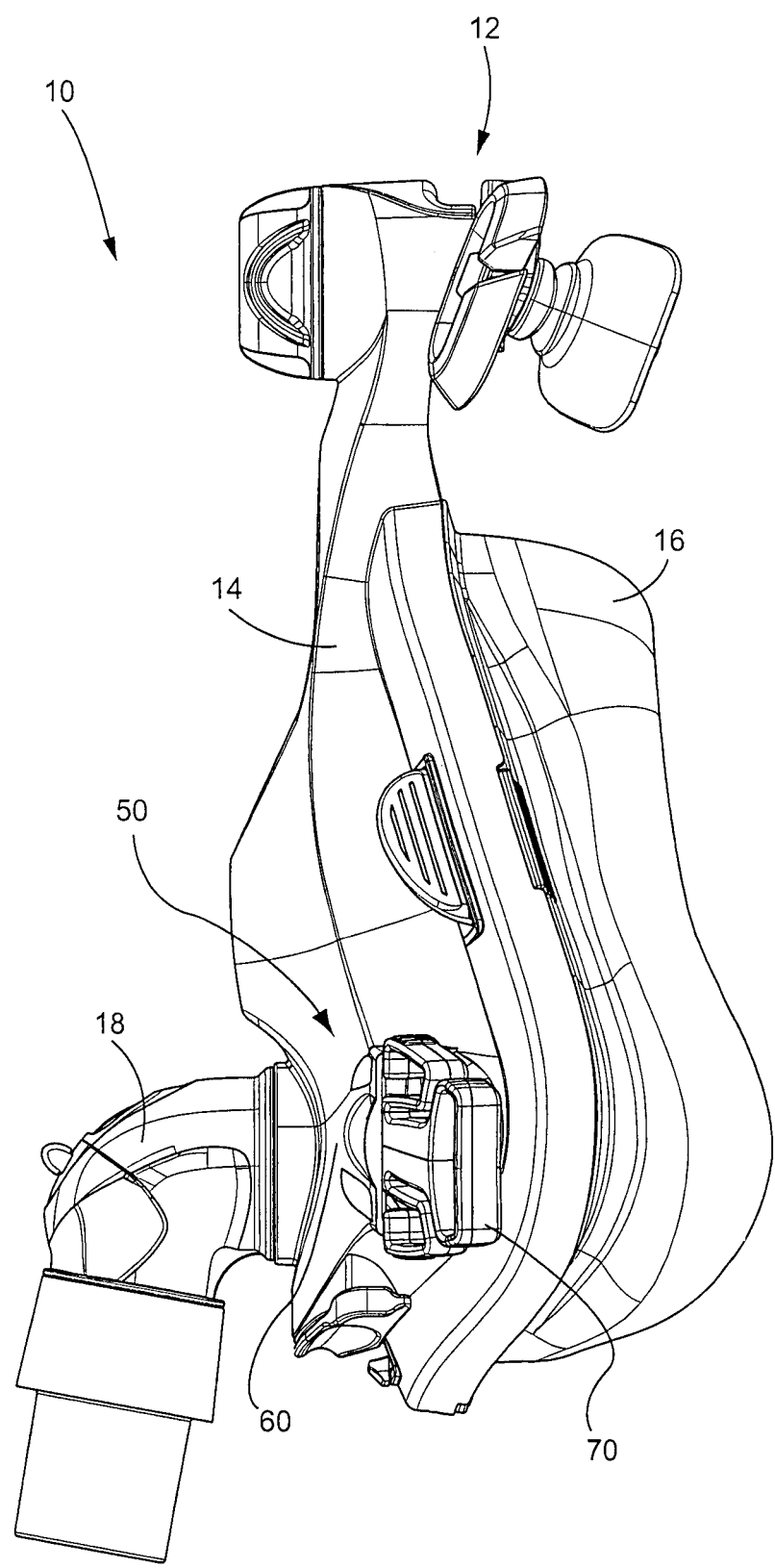

As best shown in FIGS. 3-1 to 3-2, each locking clip 70 may comprise a unitary plastic piece formed by injection molding that includes two spring arms 72, a central tab 74 between the two spring arms 72, and a cross bar 76 that forms an opening through which a lower strap of the headgear may pass and be removably connected.

Each spring arm 72 includes a locking tab 73 at a free end thereof and raised grips 75 to facilitate finger grip. In use, the locking tabs 73 are adapted to interlock with corresponding portions of the respective clip receptacle 60 with a snap-fit.

The central tab 74 is slidably insertable into a complimentary shaped portion of the clip receptacle 60. The rear side of the central tab 74 has a central channel 78 with a wide open mouth 79 that is adapted to engage a tapered rib 66 provided in the clip receptacle 60 (e.g., see FIG. 2-2).

The cross-bar 76 allows a lower strap of the headgear to be wrapped therearound. However, headgear may be attached to the locking clip 70 in other suitable manners.

2.2 Clip Receptacles

As best shown in FIGS. 2-1, 2-2, 2-3, and 4-1, each lateral side of the frame 14 includes a clip receptacle 60 structured to interlock with a locking clip 70. Each clip receptacle 60 includes a slot 62 having a central portion 64 and two locking portions 65. The locking portions 65 include a locking flange 67 (e.g., see FIGS. 1-2 and 2-3) positioned on an outer wall thereof for engagement with the locking tab 73 of a locking clip 70.

In the illustrated embodiment, an upper wall of the slot 62 includes a pair of openings 68 that are aligned with the locking flange 67. This enables the patient to visually confirm that the locking tab 73 of a locking clip 70 is interlocked with the locking flange 67 in use. Further, the openings 68 allow tooling of the undercut caused by the locking flanges 67. Also, in an embodiment, the frame 14 may be made of a clear material, e.g., clear polycarbonate, so that the patient may easily see whether the clip 70 is engaged (with or without the openings 68).

The central portion 64 includes a tapered rib 66 that extends upwardly from a lower surface towards an upper surface. The tapered rib 66 facilitates alignment of a slot 78 of the locking clip 70 with the respective clip receptacle 60.

In an embodiment of the clip receptacle 60, as shown in FIG. 2-3, $D_1$ may be about 10.0°, $D_2$ may be about 20.0 mm, $D_3$ may be about 20.0°, $D_4$ may be about 11.5°, $D_5$ may be about 3.7 mm, $D_6$ may be about 9.7 mm, and $D_7$ may be about 1.0-2.5 mm, e.g., 1.5 mm. Although specific dimensions and ranges of the clip receptacle are indicated, it is to be understood that these dimensions and ranges are merely exemplary and other dimensions and ranges are possible depending on application. For example, the exemplary dimensions may vary by 10-20% or more or less depending on application.

In the illustrated embodiment, the rib 66 has been shortened, e.g., with respect to the rib in ResMed's ACTIVA® mask. As illustrated, the tapered rib 66 is positioned entirely within the slot 62. This arrangement prevents the clip 70 from catching on the rib 66 during clip assembly. As best shown in FIG. 2-3, the rib 66 may be about 9.7 mm long (dimension $D_6$) and may be inset from the end of the receptacle by about 1.5 mm (dimension $D_7$).

A recess 80 is provided to the upper wall of the clip receptacle 60, and a lip 82 is provided adjacent to the recess 80 at the edge of the upper wall. The recess 80 and lip 82 provide tactile feedback to aid alignment during clip assembly.

Figures 1, 5:
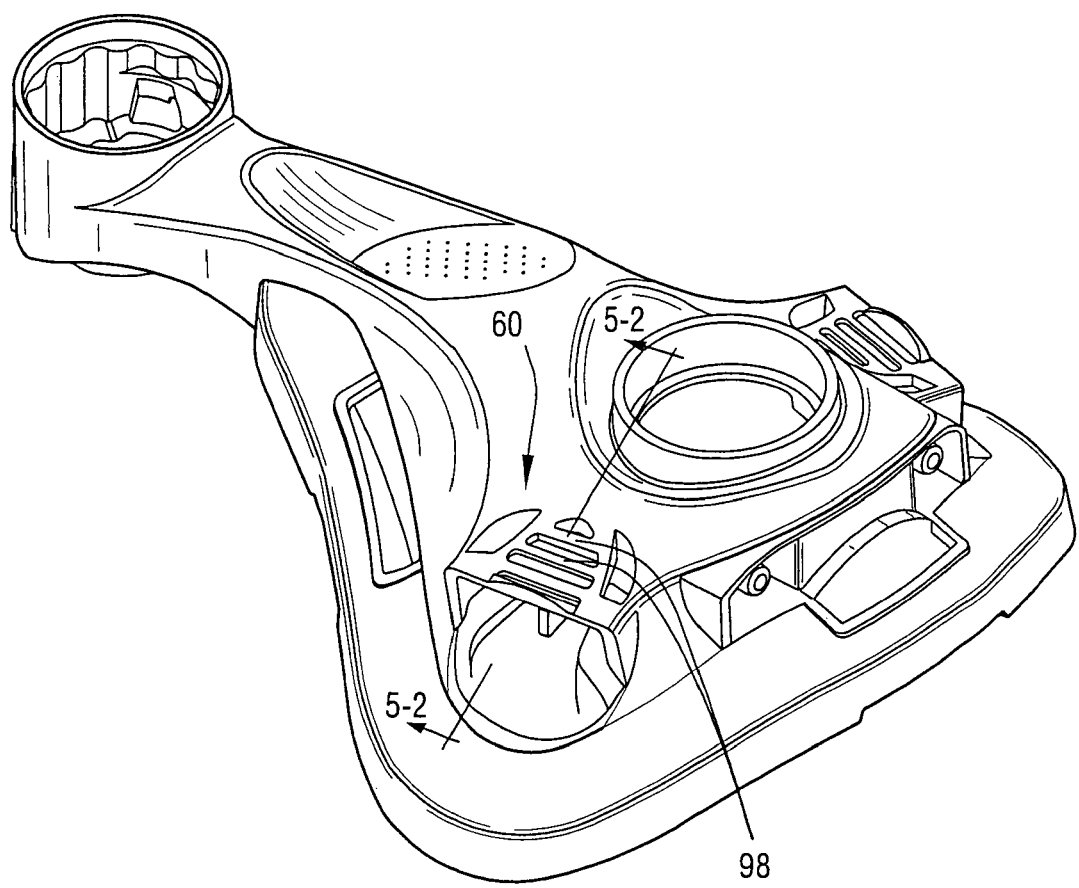
Figures 2, 5:
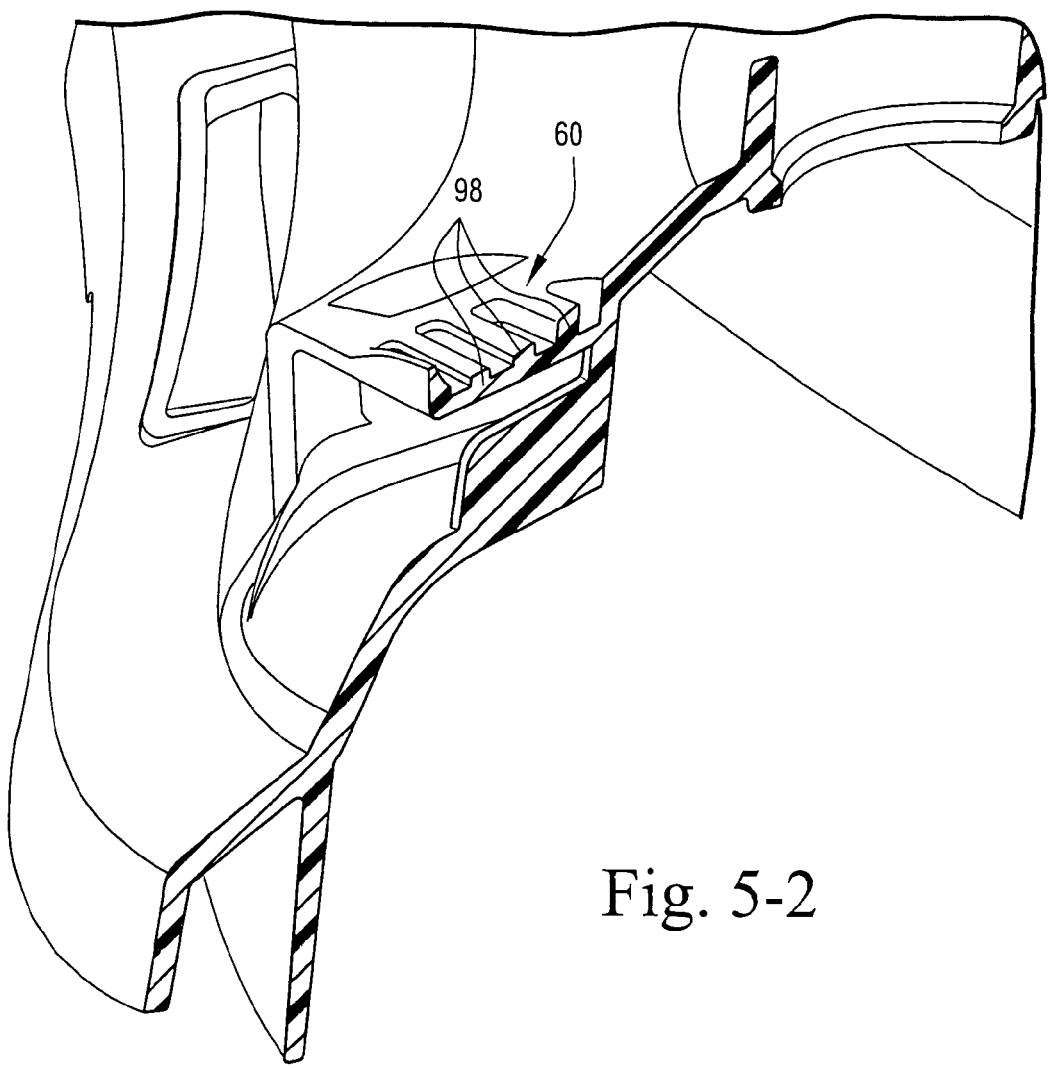

In an alternative embodiment, as shown in FIGS. 5-1 to 5-2, the upper wall of the receptacle 60 may include raised ribs 98 to enhance tactile function.

Figures 1, 2, 3, 4:
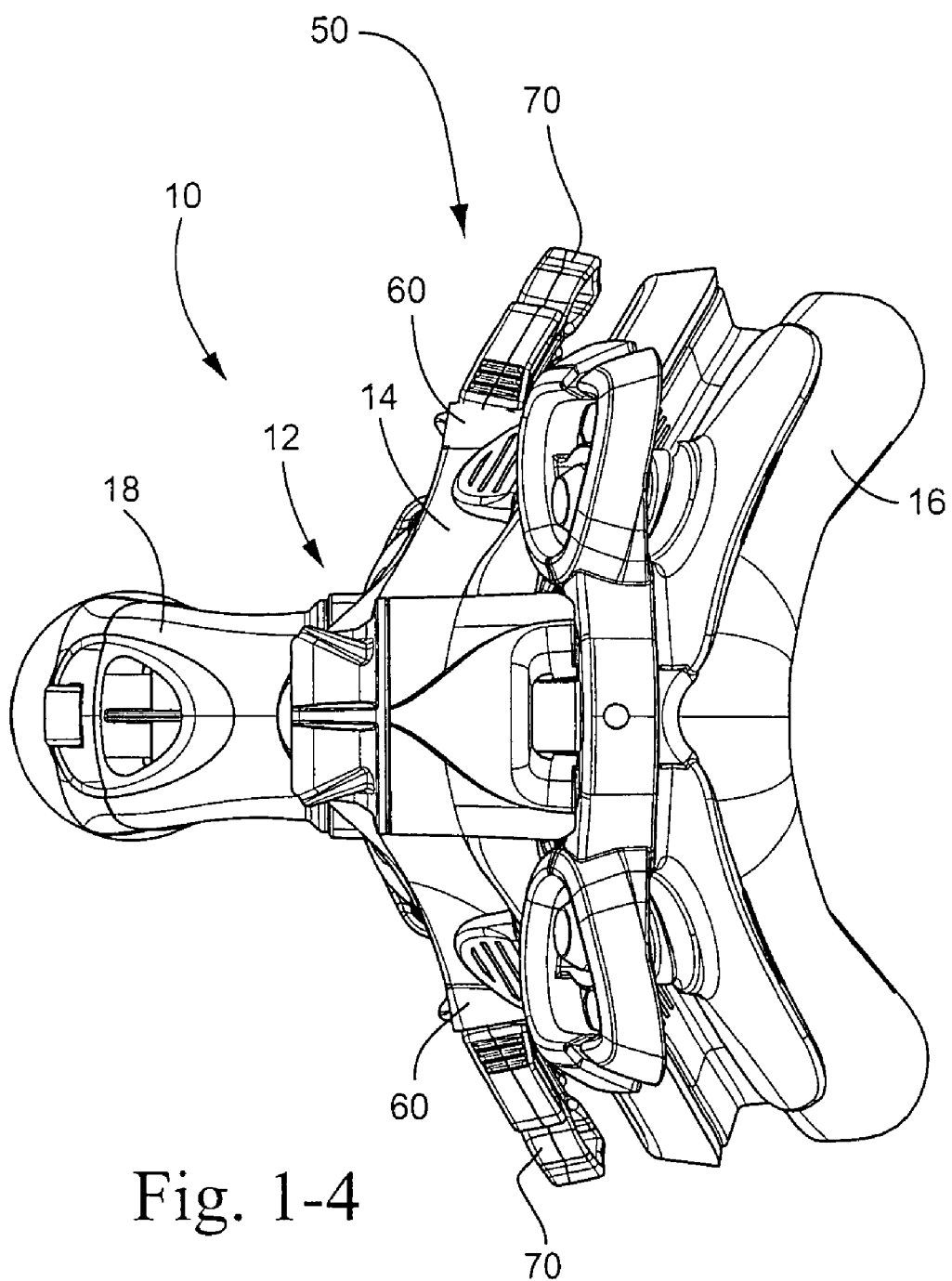
Figures 1, 2:
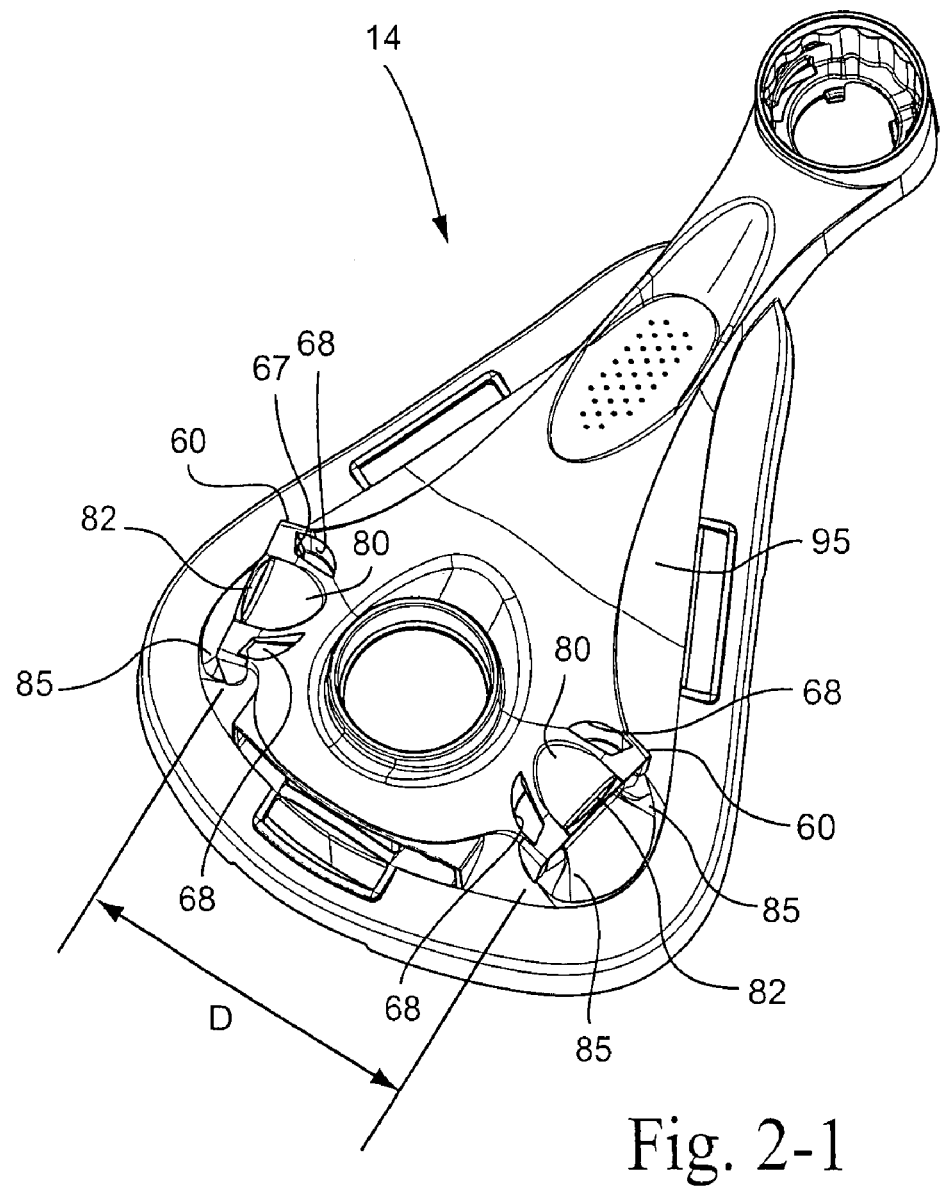
Figure 2:
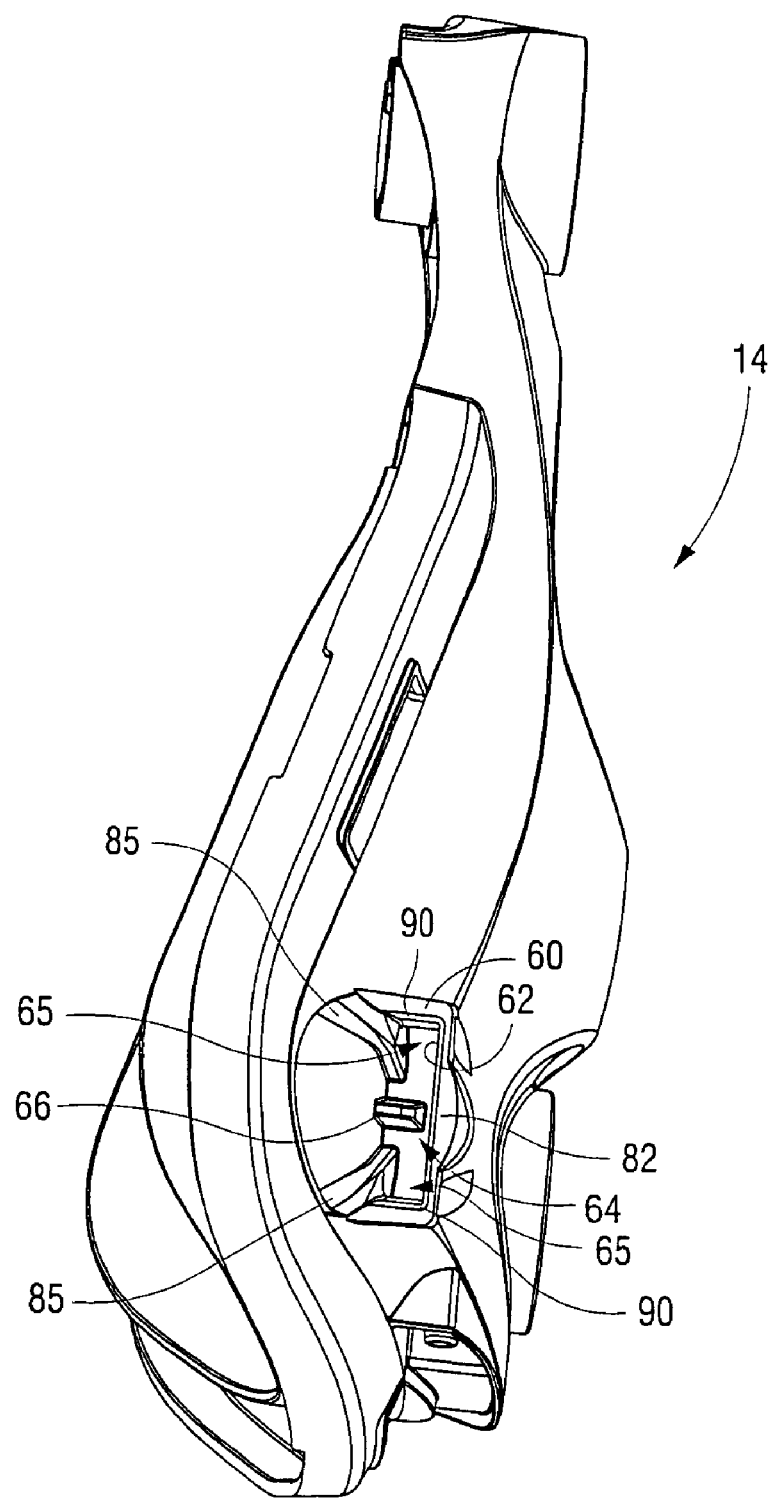
Figures 2, 3:
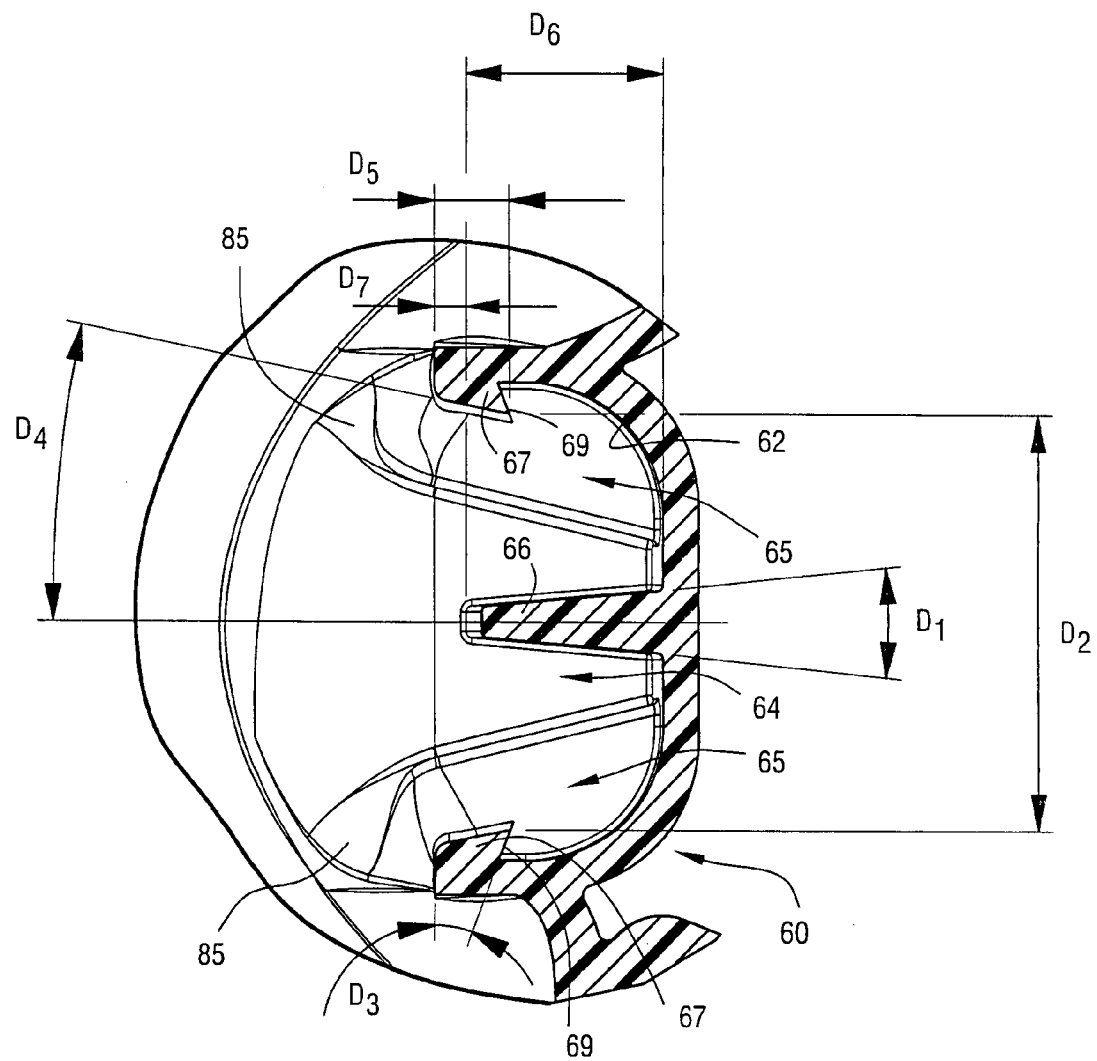
Figures 1, 3:
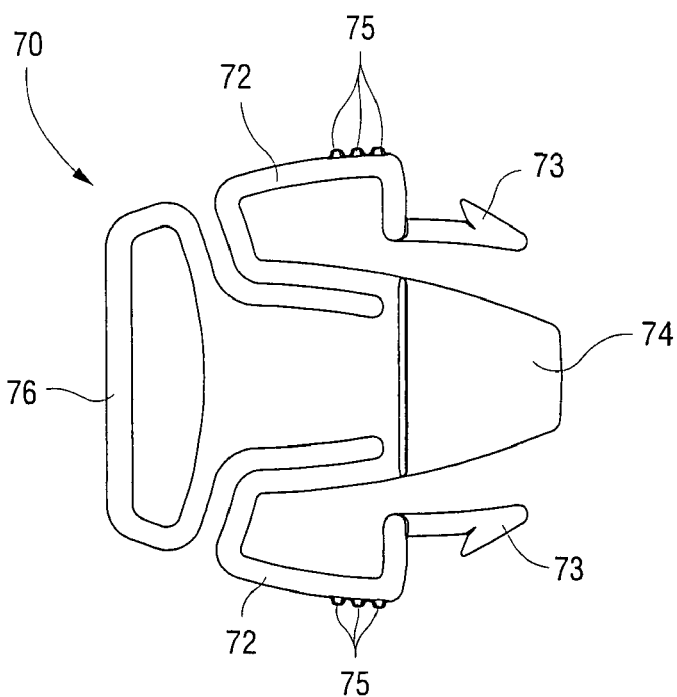
Figures 2, 3:
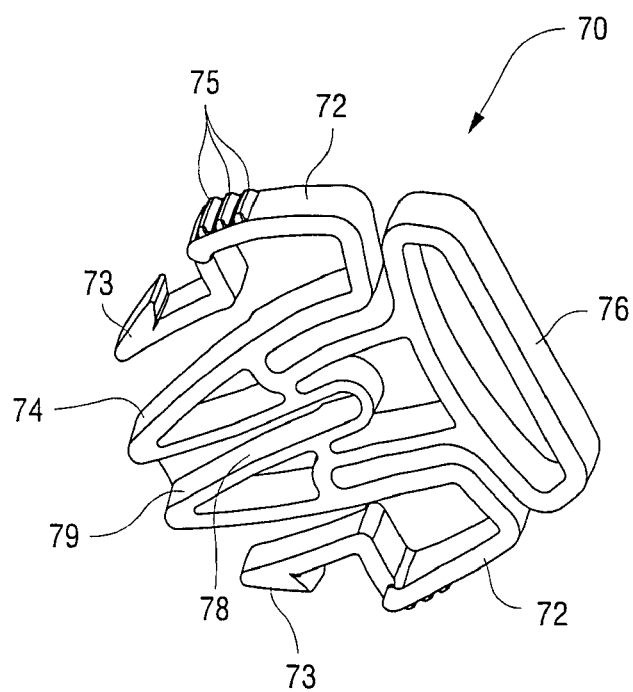
Figures 1, 4:
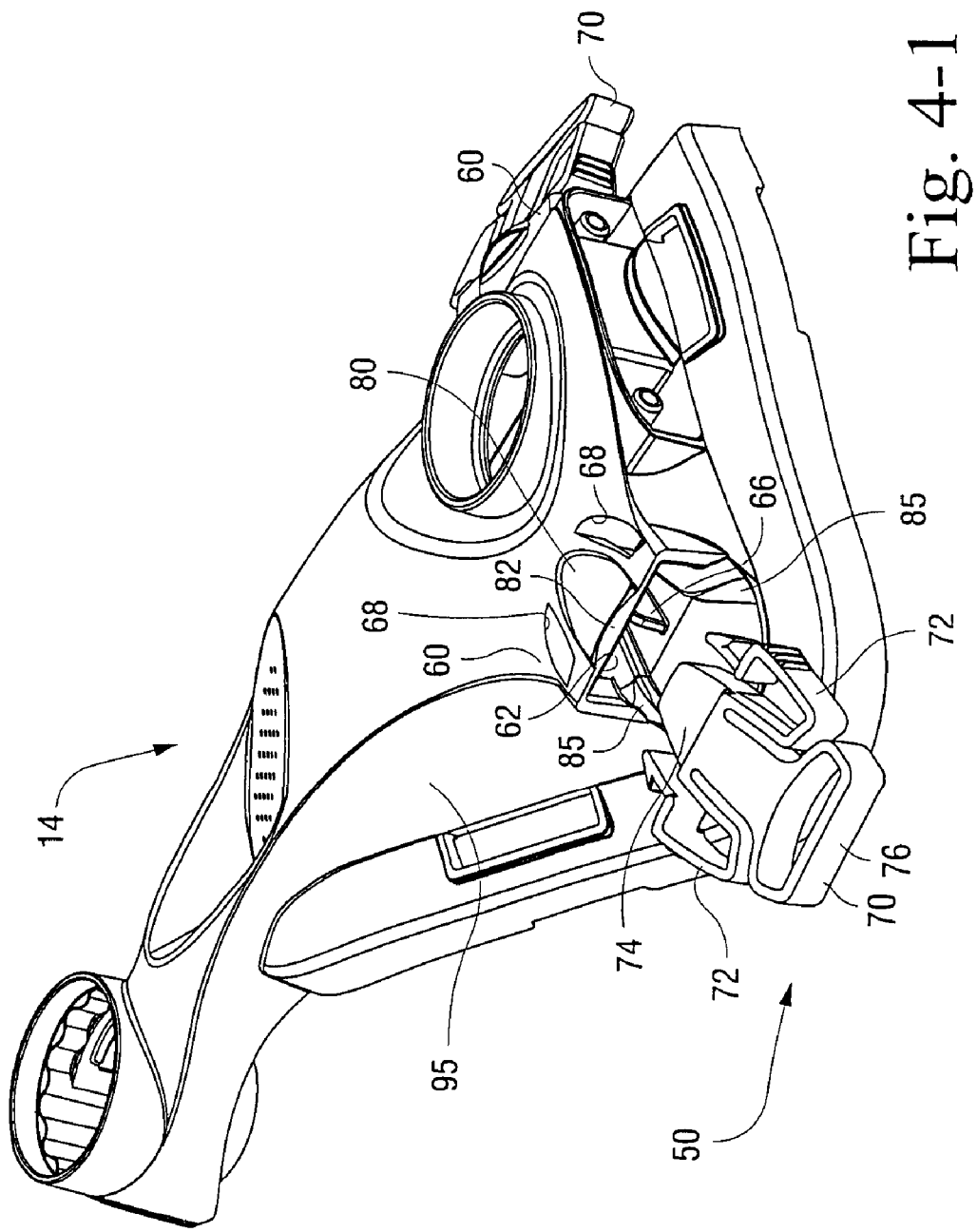
Figures 2, 4:
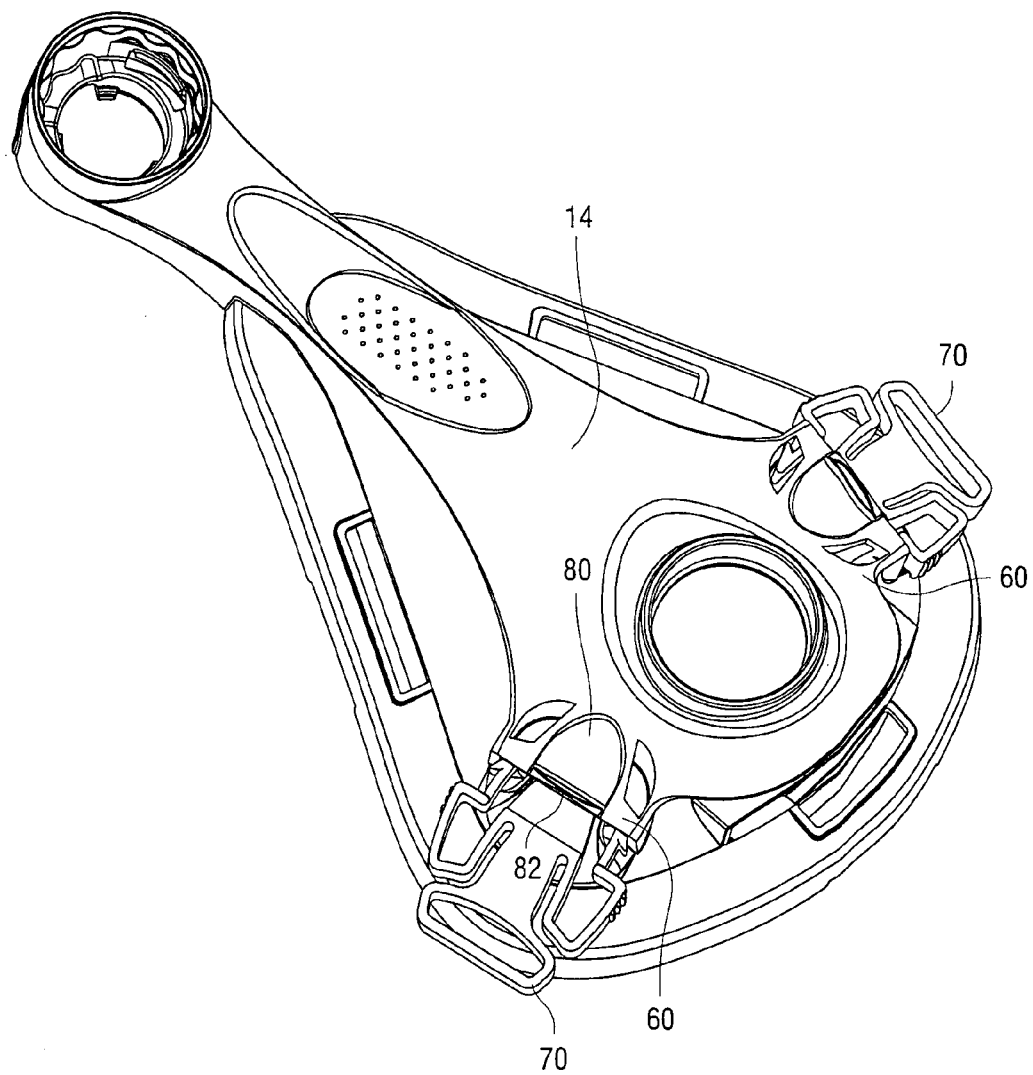
Figures 3, 4:
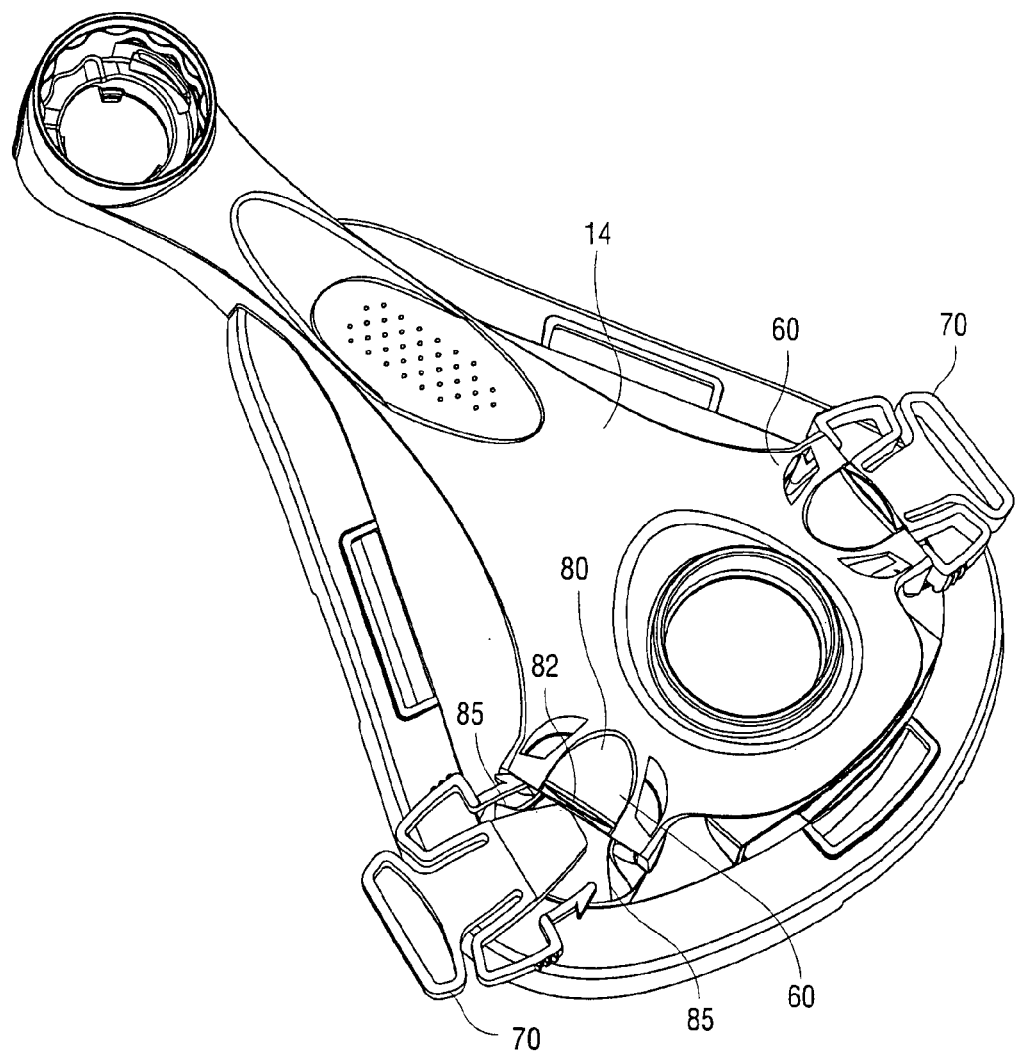
Figure 4:
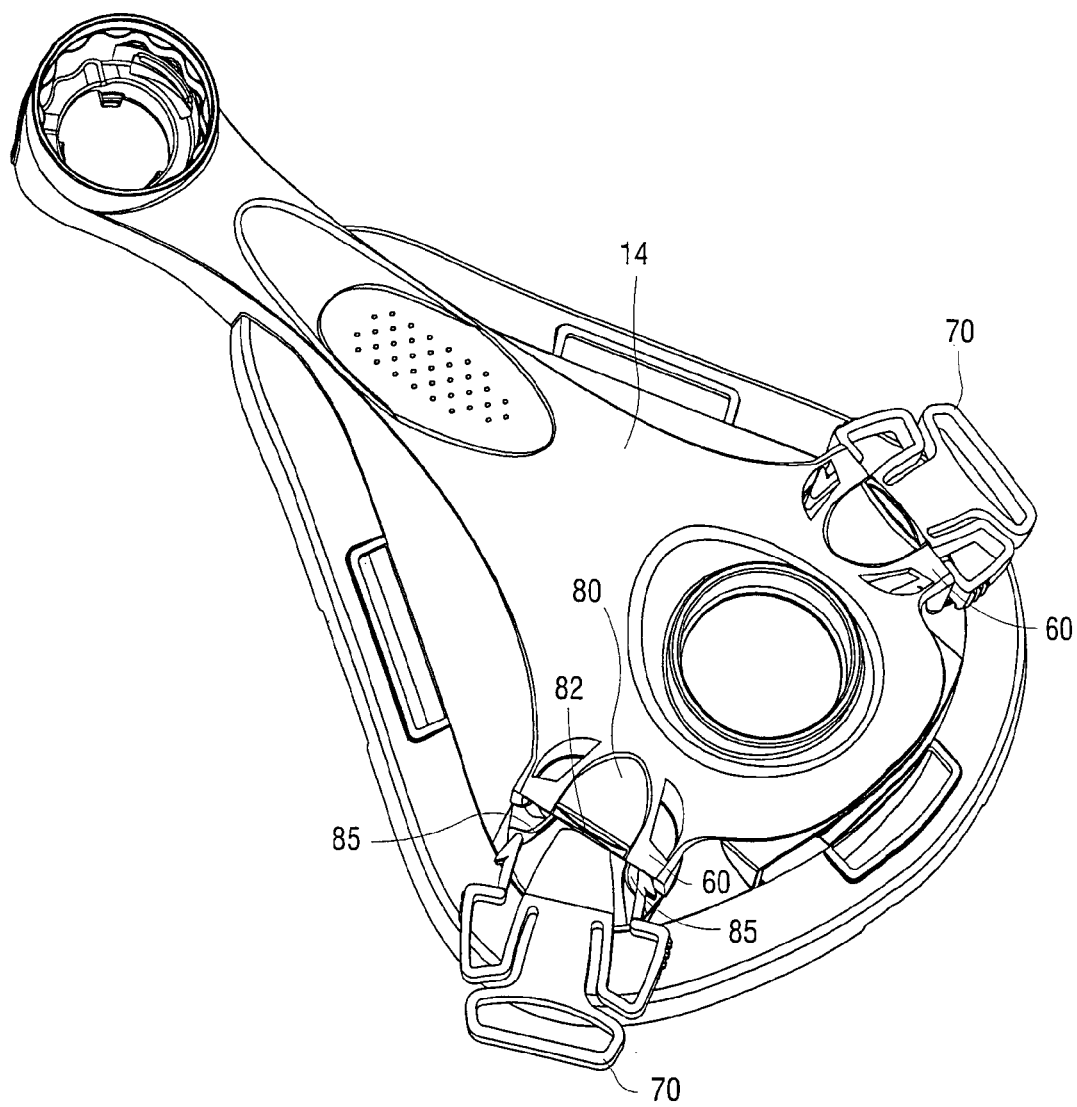

Relatively smooth external lead-ins 85 are provided on the frame 14 adjacent the entry point to the clip receptacle 60 which facilitates clip assembly, i.e., contoured guiding surfaces provided on each side of the clip receptacle 60. In use, the lead-ins 85 guide the central tab 74 of the clip into the clip receptacle 60. In addition, the frame geometry, e.g., see region 95 in FIG. 4-1, is relatively smooth and gently curved so that there is no sharp geometry to trap the clip 70 when trying to find the entry point to the clip receptacle 60.

Also, the internal draft angle 90 on each side of the clip receptacle 60 may be reduced, e.g., with respect to ResMed's ACTIVA® mask, which may improve clip retention. As best shown in FIG. 2-3, the draft angle may be about 11.5° (dimension $D_4$). Moreover, the angled back wall 69 (see FIG. 2-3) of the locking flange 67 (i.e., where the locking tab 73 of the clip 70 engages the locking flange 67) has been increased, e.g., with respect to ResMed's ACTIVA® mask, to provide better clip retention. In an embodiment, the back wall 69 may be angled about 20° (dimension $D_3$). Further, the distance across the clip receptacle 60 (i.e., between inner edges of the two locking flanges 67) is reduced, e.g., with respect to ResMed's ACTIVA® mask, which puts the clip 70 under a slight preload and keeps it more firmly in the receptacle 60. In an embodiment, the distance across the clip receptacle 60 may be about 20.0 mm (dimension $D_2$).

In addition, the distance D between the clip receptacles 60 (e.g., see FIG. 2-1) is selected so that the clips 70 are positioned relative close to one another in use to ensure that the clips 70 do not exceed the width of the cushion 16. This arrangement prevents the clips 70 from sticking into the cushion 16 or catching on the cushion 16 as the patient rolls around during use. In an embodiment, D may be about 63.5 mm. Although a specific dimension of the distance D is indicated, it is to be understood that this dimension is merely exemplary and other dimensions are possible depending on application. For example, the exemplary dimension may vary by 10-20% or more or less depending on application.

It is also noted that the clip receptacles 60 are angled relative to the frame 14. For example, the receptacles 60 slope back towards the patient's face (see FIG. 1-4), e.g., by about 10°, and the receptacle are rotated down from horizontal when viewed from the front (see FIGS. 1-2 and 2-1), e.g., by about 10°. See also U.S. patent application Ser. No. 10/838, 537, filed May 5, 2004, the entirety of which is incorporated herein by reference.

2.3 Clip Attachment

In use, each clip 70 is interlocked with a respective clip receptacle 60 by first moving the clip 70 into the respective clip receptacle 60 such that the locking tabs 73 interlock with respective locking flanges 67 with a snap fit. The clip 70 may be released from the respective clip receptacle 60 by depressing the arms 72 towards one another to clear the locking tabs 73 form respective locking flanges 67. The clip arrangement may provide audible feedback when the clips 70 are attached to the respective clip receptacles 60.

The engagement between the central channel 78 of the clip 70 and the tapered rib 66 of the clip receptacle 60 facilitate entry and assembly of the locking clip 70 into the clip receptacle 60. Also, the engagement prevents rocking or side-to-side movement between the clip 70 and clip receptacle 60.

Moreover, the clip receptacle 60 and the frame 14 provide one or more guiding surfaces to help guide the clip 70 into the respective receptacle 60, e.g., recess 80 and lip 82, lead-ins 85, and draft angle 90. For example, an error with alignment of the locking clip 70 to the clip receptacle 60 during assembly is compensated for by the lead-ins 85, i.e., lead-ins 85 allow insertion at wider range of angles as shown in FIGS. 4-1 to 4-4.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike.

What is claimed is:

1. A headgear connection assembly for a mask assembly, comprising:

a pair of clip receptacles provided to respective sides of a mask frame; and a pair of locking clips adapted to be removably interlocked with respective clip receptacles, the locking clips adapted to be removably connected to headgear straps in use, wherein each clip receptacle includes an upper wall, the upper wall having a recess extending into the upper wall and a lip adjacent to the recess that extends along an edge of the upper wall providing an entry point to the clip receptacle, the lip extending outwardly from the upper wall and away from the entry point to the clip receptacle, and wherein the mask frame includes a relatively smooth external lead-in adjacent the entry point to each clip receptacle, the lead-in including contoured guiding surfaces provided on each side of the clip receptacle that curve from outside respective sides of the clip receptacle towards a center of the clip receptacle.

2. A headgear connection assembly according to claim 1, wherein each locking clip includes two spring arms, a central tab between the two spring arms, and a cross bar that forms an opening through which a headgear strap is adapted to pass and be removably connected.

3. A headgear connection assembly according to claim 2, wherein the central tab has a central channel that is adapted to engage a tapered rib provided in the clip receptacle.

4. A headgear connection assembly according to claim 3, wherein the tapered rib is positioned entirely within the clip receptacle.

5. A headgear connection assembly according to claim 3, wherein the rib is about 9.7 mm long.

6. A headgear connection assembly according to claim 4, wherein the rib is inset from an end of the receptacle by about 1.0-2.5 mm.

7. A headgear connection assembly according to claim 6, wherein the rib is inset from an end of the receptacle by about 1.5 mm.

8. A headgear connection assembly according to claim 1, wherein each clip receptacle includes locking flanges adapted to engage respective locking tabs provided to the locking clip.

9. A headgear connection assembly according to claim 8, wherein the upper wall includes a pair of openings that are aligned with respective locking flanges.

10. A headgear connection assembly according to claim 8, wherein each locking flange includes an angled back wall adapted to engage the respective locking tab, the back wall being angled about 20° with respect to a front edge of the receptacle.

11. A headgear connection assembly according to claim 8, wherein the locking flanges include inner edges that define a distance therebetween, the distance between the inner edges being about 20.0 mm.

12. A headgear connection assembly for a mask assembly, comprising:

a pair of clip receptacles provided to respective sides of a mask frame; and a pair of locking clips adapted to be removably interlocked with respective clip receptacles, the locking clips adapted to be removably connected to headgear straps in use, wherein each clip receptacle includes an upper wall, the upper wall including two or more raised ribs each spaced apart from one another by a recess to enhance tactile function, and wherein the mask frame includes a relatively smooth external lead-in adjacent an entry point to each clip receptacle, the lead-in including contoured guiding surfaces provided on each side of the clip receptacle that curve from outside respective sides of the clip receptacle towards a center of the clip receptacle.

13. A headgear connection assembly for a mask assembly, comprising:
   a pair of clip receptacles provided to respective sides of a mask frame; and
   a pair of locking clips adapted to be removably interlocked with respective clip receptacles, the locking clips adapted to be removably connected to headgear straps in use,
   wherein each clip receptacle includes a tapered rib adapted to engage a channel provided in each clip, the rib positioned entirely within the clip receptacle, and
   wherein each clip receptacle includes an upper wall having a lip that extends along an edge of the upper wall providing an entry point to the clip receptacle, the lip extending outwardly from the upper wall and away from the entry point to the clip receptacle, and
   wherein the mask frame includes a relatively smooth external lead-in adjacent the entry point to each clip receptacle, the lead-in including contoured guiding surfaces provided on each side of the clip receptacle that curve from outside respective sides of the clip receptacle towards a center of the clip receptacle.

14. A headgear connection assembly according to claim 13, wherein the rib is inset from an end of the receptacle by about 1.0-2.5 mm.

15. A headgear connection assembly according to claim 13, wherein the rib is about 9.7 mm long.

16. A mask assembly for supplying breathable gas to a patient, the mask assembly comprising:
   a mask frame;
   a cushion provided to the mask frame;
   headgear to maintain the mask frame and cushion in a desired position on the patient's face; and
   a headgear connection assembly according to claim 1.

17. A mask assembly according to claim 16, wherein the pair of clip receptacles define a distance therebetween, the distance being selected such that the clips attached thereto do not exceed a width of the cushion.

18. A mask assembly according to claim 17, wherein the distance between the pair of clip receptacles is about 63.5 mm.

19. A mask assembly according to claim 16, wherein the frame includes a relatively smooth external lead-in adjacent an entry point to each clip receptacle.

20. A mask assembly according to claim 16, wherein the frame includes a smooth and gently curved geometry.

21. A mask assembly according to claim 16, wherein the clip receptacles are angled relative to the frame.

22. A mask assembly according to claim 21, wherein each receptacle slopes back towards the patient's face by about 10° and each receptacle is rotated down from horizontal when viewed from the front by about 10°.

23. A mask assembly for supplying breathable gas to a patient, the mask assembly comprising:
   a mask frame;
   a cushion provided to the mask frame;
   headgear to maintain the mask frame and cushion in a desired position on the patient's face; and
   a headgear connection assembly including a pair of clip receptacles provided to respective sides of the mask frame and a pair of locking clips adapted to be removably interlocked with respective clip receptacles, the locking clips adapted to be removably connected to the headgear straps in use,
   wherein the mask frame includes a relatively smooth external lead-in adjacent an entry point to each clip receptacle, the lead-in including contoured guiding surfaces provided on each side of the clip receptacle and extending from outside the clip receptacle to inside the clip receptacle, and the guiding surfaces curving from outside respective sides of the clip receptacle towards a center of the clip receptacle.

* * * * *